United States Patent [19]
Van Der Puy

[11] Patent Number: 6,013,838
[45] Date of Patent: Jan. 11, 2000

[54] CHEMICAL INTERMEDIATES BEARING A TRIFLUOROMETHYL GROUP

[75] Inventor: Michael Van Der Puy, Erie County, N.Y.

[73] Assignee: Alliedsignal Inc., Morristown, N.J.

[21] Appl. No.: 09/237,707

[22] Filed: Jan. 26, 1999

Related U.S. Application Data

[60] Provisional application No. 60/072,736, Jan. 27, 1998.

[51] Int. Cl.$^7$ ...................... C07C 249/00; C07C 251/00; C07C 257/00; C07C 263/07
[52] U.S. Cl. .......................... 564/248; 564/271; 564/279; 564/442; 564/462; 564/509; 568/35; 568/412; 568/418
[58] Field of Search ..................................... 564/248, 271, 564/279, 442, 462, 509; 568/418, 35, 412

[56] References Cited

U.S. PATENT DOCUMENTS

| | | |
|---|---|---|
| 4,638,091 | 1/1987 | Bowden . |
| 5,446,217 | 8/1995 | Van Der Puy . |
| 5,654,473 | 8/1997 | Van Der Puy . |

OTHER PUBLICATIONS

Journal of The Chemical Society Perkin Transactions I; "The Peroxide–initiated Addition of 1,1–Dibromotetrafluoroethane to Ethylene, Propene, and 2–Methylpropene" JCPRB4(Sep. 10) 1121–1290(1972).

Principles of Chemistry, "Chemical Properties of the Noble Glass" Raymond E. Davis, 1938.

Journal of Flourine Chemistry, 76 (1996) 49–54 "Preparation, Fluorination and Synthetic Utility of a CFC–Olefin Adduct", Michael Van Der Puy, et al.

Tetrahedron Letters, vol. 32, No. 26, pp. 3071–3074, 1991 "Synthesis of Trifluoromethylalkenes and Alkynes. Trifluoromethyl Captodative Olefins", Andre J. Laurent, et al.

Bull. Chem. Soc. Jpn., 60, 4385–4394 (1987), "Practical, Stereocontrolled Synthesis of Polyfluorinated Artificial Pyrethroids", Makoto Fujita, et al.

J. Org. Chem. 1994, 59, 5692–5699, "New Method for Trifluoromethylation of Enolate Anions and Applications to Regio–,Diastereo–and Enantioselective Trifluoromethylation", Teruo Umemoto, et al.

Tetrahedron Letters, vol. 34, No. 36, pp. 5711–5714, 1993 "Trifluoroethylidenation of Compounds with Activated Methylene Groups", Celal Ates, et al.

Tetrahedron Letters, vol. 33, No. 9, pp. 1221–1224, 1992 Trifluoroacetyltriphenylsilane as a Potentially Useful Fluorine–Containing Building Block. Preparation and its Transformation into 2,2–Difluoro Enol Silyl Ethers, Fuqiang Jin.

Tetrahedron Letters, vol. 33, No. 4 pp. 511–514 1992, Palladium–Catalyzed Cross–Coupling of Trifluoroisopropenylzinc Reagent with Vinyl Halides. A Novel Stereospecific Synthesis of Trifluoromethylated 1,3—Dienes, Biao Jiang, et al.

1989 Bull. Chem. Soc. Jpn., 62, 1352–1354 (1989) vol. 62, No. 4, "A Facile and practical Synthesis of 1–Aryl–3,3, 3–trifluoropropynes", Tamejiro Hiyama, et al.

Derwent Publications Ltd., 1–Substd.–2–Chloro–3,3,3–Trifluoropropene–by Reactive e.g. 1–(Chlorophenyl)–Dichlorotri Fluoro Propyl Acetate with Zinc Powder in Aprotic Solvent JP 62228032 A, 871006, 8745.

*Primary Examiner*—Samuel Barts
*Attorney, Agent, or Firm*—Colleen D. Szuch; Jay P. Friedenson; Marie Collazo

[57] ABSTRACT

Novel trifluoromethylated intermediates are provided which are useful in synthesizing trifluoromethylated organic compounds. Specifically, compounds of the formula $CF_3CR$ are provided, wherein R is $(Cl)=CHCH_2SO_2Ph$, $(Cl)=CHCH_2CH_2C(=O)CH_3$, $(Cl)=CHCH_2CH(COCH_3)_2$, $(Cl)=CHCH_2NR'R''$ or $H=CHCH=NR'$; R' and R" are the same or different and are selected from the group consisting of hydrogen, unsubstituted or substituted $C_1$ to $C_6$ straight chain or branched alkyl, unsubstituted or substituted $C_3$ to $C_7$ cycloalkyl, unsubstituted or substituted $C_2$ to $C_{12}$ alkenyl, a benzyl group unsubstituted or substituted with R'", or a phenyl group unsubstituted or substituted with R'"; or R' and R" taken together form a five- or six-membered ring; and R'" is an unsubstituted or substituted $C_1$ to $C_6$ straight chain or branched alkyl, an unsubstituted or substituted $C_1$ to $C_6$ alkoxy, an unsubstituted or substituted $C_1$ to $C_6$ thioakyl, a cyano, a halogen, or a $C_1$ to $C_2$ dialkylamino group; with the proviso that when the alkyl, cycloalkyl or alkenyl of R' or R" or the alkyl, alkoxy or thioalkyl of R'" is substituted, it may be substituted with any group compatible with amine functionality. The novel compounds are versatile intermediates for the synthesis of a wide variety of trifluoromethylated organic compounds, which have found great utility as pharmaceuticals, agricultural chemicals, and materials such as liquid crystals.

26 Claims, No Drawings

CHEMICAL INTERMEDIATES BEARING A TRIFLUOROMETHYL GROUP

CROSS REFERENCE TO RELATED APPLICATION

Reference is made to and priority claimed from pending Provisional Patent Application Serial No. 60/072,736 filed Jan. 27, 1998.

FIELD OF THE INVENTION

The present invention relates to novel trifluoromethylated intermediates useful in the synthesis of trifluoromethylated organic compounds, particularly compounds bearing the trifluoromethyl group in addition to convenient functionality, e.g., carbonyl, sulfonyl, imine, hydroxyl, and amine functional groups.

BACKGROUND

Fluorinated organic compounds, specifically trifluoromethylated organic compounds, have found great utility as pharmaceuticals, agricultural chemicals, and materials such as liquid crystals. One major route for the synthesis of these organofluorine compounds utilizes trifluoromethylated intermediates.

A number of such trifluoromethylated intermediates and processes for their synthesis have been disclosed. See, for example, Fujita et al., "Practical Stereocontrolled Synthesis of Polyfluorinated Artificial Pyrethroids", 60 *Bull. Chem. Soc. Jpn.* 4385 (1987); Hiyama et al., "A Facile and Practical Synthesis of 1-Aryl-3,3,3-Trifluoropropynes",62 *Bull. Chem. Soc. Jpn.* 352 (1989); and Laurent et al., "Synthesis of Trifluoromethylalkenes and Alkynes. Trifluoromethyl Captodative Olefins", 32 *Tetrahedron Letters* 307 (1991). Commonly assigned U.S. Pat. No. 5,654,473 discloses trifluoromethylated intermediates of the formula $CF_3CCl=CHCH_2X$ wherein X is hydrogen, fluorine, bromine, iodine, $OC(=O)CH_3$ or hydroxyl.

Despite the aforementioned disclosures, there exists a continuing need for the development of versatile intermediates from which trifluoromethylated organic compounds may be prepared. The novel trifluoromethylated compounds of the present invention meet the need for such intermediates by providing compounds with convenient functionality in addition to the trifluoromethyl group.

SUMMARY OF THE INVENTION

The present invention provides trifluoromethylated compounds of the general formula:

$$CF_3CR$$

wherein R is $(Cl)=CHCH_2SO_2Ph$, $(Cl)=CHCH_2CH_2C(=O)CH_3$, $(Cl)=CHCH_2CH(COCH_3)_2$, $(Cl)=CHCH_2NR'R''$ or $H=CHCH=NR'$; R' and R'' are the same or different and are selected from the group consisting of hydrogen, unsubstituted or substituted $C_1$ to $C_6$ straight chain or branched alkyl, unsubstituted or substituted $C_3$ to $C_7$ cycloalkyl, unsubstituted or substituted $C_2$ to $C_{12}$ alkenyl, a benzyl group unsubstituted or substituted with R''', a phenyl group unsubstituted or substituted with R''' or R' and R'' taken together form a five- or six-membered ring; and R''' is an unsubstituted or substituted $C_1$ to $C_6$ straight chain or branched alkyl, an unsubstituted or substituted $C_1$ to $C_6$ alkoxy, an unsubstituted or substituted $C_1$ to $C_6$ thioakyl, a cyano, a halogen, or a $C_1$ to $C_2$ dialkylamino group; with the proviso that when the alkyl, cycloalkyl or alkenyl of R' or R'' or the alkyl, alkoxy or thioalkyl of R''' is substituted, it is substituted with any group compatible with amine functionality.

The compounds of the present invention are particularly useful and versatile intermediates for the synthesis of organofluorine compounds because they contain a trifluoromethyl group and a reactive functional group. Certain of the instant trifluoromethylated compounds also contain a $C(Cl)=CH$ group, which is a latent, or masked, carbonyl group. The presence of one or more of these groups provides the intermediates of the present invention with ample functionality for their further chemical transformation.

DESCRIPTION OF THE PREFERRED EMBODIMENTS

The trifluoromethylated compounds of the present invention are of the general formula:

$$CF_3CR$$

wherein R is $(Cl)=CHCH_2SO_2Ph$, $(Cl)=CHCH_2CH_2C(=O)CH_3$, $(Cl)=CHCH_2CH(COCH_3)_2$, $(Cl)=CHCH_2NR'R''$ or $H=CHCH=NR'$; R' and R'' are the same or different and are selected from the group consisting of hydrogen, unsubstituted or substituted $C_1$ to $C_6$ straight chain or branched alkyl, unsubstituted or substituted $C_3$ to $C_7$ cycloalkyl, unsubstituted or substituted $C_2$ to $C_{12}$ alkenyl, a benzyl group unsubstituted or substituted with R''', a phenyl group unsubstituted or substituted with R''' or R' and R'' taken together form a five- or six-membered ring; and R''' is an unsubstituted or substituted $C_1$ to $C_6$ straight chain or branched alkyl, an unsubstituted or substituted $C_1$ to $C_6$ alkoxy, an unsubstituted or substituted $C_1$ to $C_6$ thioakyl, a cyano, a halogen, or a $C_1$ to $C_2$ dialkylamino group; with the proviso that when the alkyl, cycloalkyl or alkenyl of R' or R'' or the alkyl, alkoxy or thioalkyl of R''' is substituted, it is substituted with any group compatible with amine functionality. As used herein, compatible with amine functionality means that the functionality does not react with the amino group under the conditions used in the reaction with HCFC-1343. By way of example, without limitation, alkoxy, trifluoromethyl, alkenyl, ketal, and acetal are considered groups that are compatible with amine functionality. One skilled in the art will be able to readily identify other suitable substitutions.

The novel chemical intermediates of the present invention have the common feature that they all can be prepared from the same raw material, namely 1,3-dichloro-4,4,4-trifluorobut-2-ene ($CF_3C(Cl)=CHCH_2Cl$) or HCFC-1343. Alternatively, they may be prepared from the corresponding iodide ($CF_3CCl=CHCH_2I$) or bromide ($CF_3CCl=CHCH_2Br$). Preparation of the compounds of the present invention proceeds by the general reaction:

$$CF_3C(Cl)=CHCH_2X+Z \rightarrow CF_3C(Cl)=CHCH_2Z+X$$

wherein Z represents the nucleophile, and X represents a halogen (Cl, Br, or I).

As described in U.S. Pat. No. 5,654,473, herein incorporated by reference in its entirety, HCFC-1343 may be prepared by passing 1,3,3-trichloro-4,4,4-trifluorobutane (HCFC-353) over a catalyst at a temperature of about 285° C. Specifically, the catalyst is charged to a reactor, heated to about 285° C. under a nitrogen flow, and HCFC-353 is fed into the reactor. Contact times are from about 1 second to about 60 seconds, preferably from about 5 seconds to about 20 seconds. Pressure is not critical. Conversions for this process are approximately 50%. Useful catalysts for the preparation of HCFC-1343 include, without limitation, metal oxides such as chrome (III) oxide, supported metal oxides such as chrome (III) oxide supported on aluminum oxide or carbon, and supported metal halides such as cobalt (II) chloride and nickel (II) chloride supported on carbon, aluminum oxide, aluminum fluoride, or a mixture of such supported materials, such as a mixture of $Cr_2O_3$ and $Al_2O_3$. Chrome (III) oxide is preferred due to its level of reactivity and commercial availability. Suitable chrome (III) oxide catalysts are available from Mallinckrodt Specialty Chemicals Co., St. Louis, Mo. One of ordinary skill in the art can readily optimize the conditions of the reaction, without undue experirnentation, to obtain HCFC-1343.

HCFC-353 may be produced in the presence of a catalyst and an inert solvent by an addition reaction of ethylene and 1,1,1-trichloro-2,2,2-trifluoroethane, as described in U.S. Pat. No. 5,532,419, herein incorporated by reference in its entirety. Any commercially available catalyst known in the art to be useful in catalyzing the addition of halocarbons to olefins may be employed. Suitable addition catalysts include, without limitation, copper (I) salts such as cuprous chloride and cuprous iodide, iron (II) salts such as ferrous chloride and ferrous acetate, and metal carbonyls such as iron carbonyl and cobalt carbonyl. Cuprous chloride is preferred. Optionally, any well-known co-catalyst useful in catalyzing the addition of halocarbons to olefins may be employed in the reaction. Suitable addition co-catalysts include aliphatic or aromatic amines such as pyridine and diethylamine.

The corresponding iodide starting material ($CF_3CCl$=$CHCH_2I$) may be prepared by reacting sodium iodide and HCFC-1343 in an at least about 1:1 molar equivalent ratio in a solvent, as described in U.S. Pat. No. 5,654,473. The preferred solvent is acetone because sodium iodide is appreciably soluble, while the byproduct sodium chloride is appreciably insoluble. The corresponding bromide is prepared in a similar manner.

The trifluoromethylated intermediates of the present invention are prepared using HCFC-1343 in either one or two reaction steps. In general, the HCFC-1343 and the nucleophile are dissolved in a solvent and reacted. Any inert solvent miscible with the halocarbon and nucleophile may be used. Exemplary solvents are, without limitation, low molecular weight alcohols such as methanol and ethanol, amides such as dimethylformamide (DMF), ketones such as acetone, sulfolane, and dimethylsulfoxide (DMSO). Preferably, the solvent is methanol, acetone, or DMF, which are inexpensive and readily available solvents.

Reactions of the type utilized for the production of the claimed trifluoromethylated intermediates of the present invention are known. Further, reaction conditions for the production of the claimed intermediates can be readily determined by one of ordinary skill in the art. The conditions will depend upon the nucleophile and solvent utilized. In general, the HCFC-1343 and nucleophile are reacted at a temperature from about 25° C. to about 150° C. or up to the boiling point of the solvent. The period of reaction is generally from about several minutes to about several days. The pressure at which the reaction is carried out is, generally, not critical.

The phenylsulfonyl intermediate ($CF_3C(CI)$=$CHCH_2SO_2Ph$) of the present invention is conveniently prepared by refluxing a mixture of sodium benzenesulfinate and HFC-1343 in methanol. Reaction times are in the range of about 5 to about 20 hours. As the iodide ($CF_3CCl$=$CHCH_2I$) reacts more rapidly with nucleophiles than the corresponding chloride, the iodide, prepared in situ by the addition of a small amount (e.g., about 2–10 mol %) of sodium or potassium iodide, often serves to catalyze the displacement reaction. While the stoichiometric mole ratio of reactants is about 1:1, a slight excess may be beneficial for the purpose of improving conversion without excessively long reaction times. Thus, mole ratios of about 1 to about 2 are preferred, and ratios of about 1.1 to about 1.5 are most preferred.

In the case of the acetyl intermediate ($CF_3CCl$=$CHCH_2CH_2C(=O)CH_3$), HCFC-1343 is treated with a salt of acetylacetone, such as the lithium, sodium, or potassium salt. The lithium salt is commercially available, but it can be prepared by reacting acetylacetone with a suitable base such as sodium methoxide, potassium hydroxide and the like. Salts of acetylacetone are soluble in water, but as the HCFC-1343 is not, a mixture of water and a lower alkanol makes a good reaction solvent, dissolving both reactants. As with the sulfonate intermediate, the stoichiometric mole ratio of reactants is about 1:1, but ratios of about 1 to about 2 are preferred, and ratios of about 1.1 to about 1.5 most preferred. It is believed that the initial reaction product is $CF_3CCl$=$CHCH_2CH(COCH_3)_2$, which is further transformed by the action of base to give the product ketone. Some deacylation may occur in the initial reaction with the salt of acetylacetone, so that the crude material may be a mixture of $CF_3CCl$=$CHCH_2CH(COCH_3)_2$ and $CF_3CCl$=$CHCH_2CH_2C(=O)CH_3$. To insure complete reaction, the crude product is treated with aqueous base (e.g., about 5–25% aqueous KOH or NaOH) for a short time (about 0.5 to about 2 hours) at or near reflux. The procedure can be readily adapted to other active methylene (1,3-dicarbonyl) compounds such as malonate esters.

For the amine intermediates ($CF_3CCl$=$CHCH_2NR'R''$), HCFC-1343 is treated with either a primary or a secondary amine, in a stoichiometric ratio of about 2 moles of amine per mole of HCFC-1343. In a typical preparation using a secondary amine, the amine and HCFC-1343 are reacted together in a molar ratio of at least about 2:1 to about 2.5:1 in a suitable solvent. Suitable secondary amines include dimethylamine, ethylmethylamine, diethyl amine, di-n-propylamine, benzylmethylamine, N-benzylpropylamine, N-methylaniline, pyrrolidine and piperidine, all of which are commercially available. Diethylamine, benzylmethylamine and piperidine are preferred. As will be appreciated by one skilled in the art, substituted secondary amines may also be used as long as the substituted group is compatible with amine functionality. A non-limiting example of a suitable substituted secondary amine is N-methyl-2,2,2-trifluoroethylamine, which may be prepared by the method disclosed in, for example, U.S. Pat. No. 4,638,091. Other suitable substituted secondary amines will occur readily to those skilled in the art.

Suitable solvents are polar or aprotic solvents such as DIF or DMSO. Optionally a co-solvent such as ether may be employed. Due to undesirable side reactions that occur at elevated temperatures, the reaction temperature for both amine and imine (described below) in the preferred solvent DMF, are room temperature or slightly above (i.e. from about 20 to about 50° C.). When the reaction is complete, the mixture is treated with aqueous base to convert amine salts (including those of the product) to the free amine. The amine product is then separated by any convenient means such as phase separation or extraction, followed by a purification procedure appropriate to the specific amine product (e.g., distillation or chromatography).

For the preparation of $CF_3CCl$=$CHCH_2NR'R''$ using a primary amine (i.e. when R''=H), the reaction stoichiometry and general procedure to be used is the same as described above. However, in this case, it is preferable to use reactant ratios closer to the stoichiometric value of 2 moles of amine per mole of HCFC-1343. More care must also be given to the reaction time. The reason is that with primary amines, the reaction can proceed further, especially in the presence of excess amine to the imine intermediates of this invention. Thus, the imine intermediates ($CF_3CH=CHCH=NR'$) of this invention are made in an exactly analogous manner, using a primary amine and HCFC-1343 in a stoichiometric ratio of 3 moles of amine per mole of HCFC-1343. Suitable primary amines include ammonia, methylamine, ethylamine, n-propylamine, isopropylamine, n-butylamine isobutylamine, sec-butylamine, tert-butyl amine, n-amylamine, n-hexylamine, cyclohexylamine, benzylamine, α-phenylethylamine, β-phenylethylamine, allyl amine, aniline, toluidine, anisidine, p-chloroaniline, m-bromoaniline, m-phenylenediamine, or p-phenylenediamine, all of which are commercially available. Tertiary butyl amine, allyl amine, and benzylamine are preferred. As will be appreciated by one skilled in the art, substituted amines may also be used as long as the substituted group is compatible with amine functionality. A non-limiting example of a suitable substituted primary amine is trifluoroethylamine, which may be prepared by the method disclosed in, for example, U.S. Pat. No. 4,638,091. Other suitable substituted primary amines will occur readily to those skilled in the art.

Control of the reaction, so as to obtain either the amine or the imine, can be accomplished primarily by the reaction stoichiometry. As discussed above, at a ratio of amine to HCFC-1343 of about 2 to about 3, preferably about 2 to about 2.3, the amine species is predominantly produced; while at a ratio of at least about 3, preferably about 3 to about 4, the imine species is predominantly produced. The reaction can also be controlled by the reaction time, which is somewhat longer for the imine (about 3 to about 6 days) than the amine (about 1 to about 3 days). For the amine, a trade-off may be required between selectivity and conversion.

The optimum reaction time needed to maximize the formation of the amine product will be different for different amines since they will react at different rates, but this can be determined experimentally. Test reactions can be conducted on a small scale at different amine/HFCF-1343 ratios and the concentration of amine product may be plotted vs. time. Generally, however, as noted above, the formation of imine is notably slower, and requires 3 moles of amine per mole of HCFC-1343, so that it is fairly easy to obtain either amine or imine as the principle product.

One of ordinary skill in the art will recognize that the trifluoromethylated compounds of the present invention are useful as intermediates for the preparation of a wide variety of organofluorine compounds. Exemplary of such organofluorine compounds are, without limitation, trifluoromethylated alcohols, alkynes, aldehydes, esters, amines, and sulfur compounds. Such trifluoromethylated organic compounds are used in or as pharmaceuticals, agricultural chemicals, and liquid crystals.

For example, it has been shown that the CCl=CH group can be reduced to the $CH_2CH_2$ group. Thus, the acetyl ($CF_3C(Cl)=CHCH_2C(=O)CH_3$) intermediate made here is viewed as a raw material for $CF_3CH_2CH_2CH_2CH_2CH(OH)CH_3$ (7,7,7,-trifluoro-2-heptanol) via reduction. Trifluoromethyl alcohols are materials of considerable commercial importance (e.g., $CF_3CH_2OH$, $CF_3CH(OH)CH_3$ and $CF_3CH(OH)CF_3$).

It is to be noted that there is no Cl in the N-(4,4,4-trifluorobutenylidene)-t-butylamine intermediate of the present invention. This compound is an example of an imine, despite the IUPAC nomenclature. Imines give aldehydes or ketones on hydrolysis. Thus, hydrolysis of this intermediate should give $CF_3CH=CHCHO$.

The intermediates of the present invention, their preparation and use will be clarified further by a consideration of the following examples.

EXAMPLE 1

Preparation of 1-(phenylfulfonyl)-4,4,4-trifluoro-3-chlorobut-2-ene ($CF_3CCl=CHCH_2SO_2Ph$)

A solution of 18 g (0.067 mol) $CF_3CCl=CHCH_2Cl$ and 20 g (0.122 mol) sodium benzenesulfinate in 100 mL methanol was refluxed for 17 hours. The solution was then concentrated on the rotovap and the residue treated with 250 mL water. The crude yellow solid was washed with water and air dried (18.6 g). Pure $PhSO_2CH_2CH=CClCF_3$, m.p. 86–87° C., was obtained as a white solid after two recrystallizations from 60% ethanol-water (14.9 g). $^1$H NMR: δ 7.9 (2H); 7.7 (1H); 7.6(2H); 6.57 (t, 1H); 4.1 (2H) ppm. $^{19}$F NMR: −70.1 ppm. IR (cm$^{-1}$); 3065; 2988; 2945; 1659; 1320; 1154. Analysis: Calc. For $C_{10}H_8ClF_3O_2S$ (284.68): C, 42.19%; H, 2.83%. Found: C, 42.08; H,2.92%.

EXAMPLE 2

Preparation of 7,7,7-Trifluoro-6-chloro-hept-5-en-2-one ($CF_3CCl=CHCH_2CH_2C(=O\ CH_3)$)

Lithium acetylacetonate (7.0 g, 0.066 mol) was dissolved in 50 mL methanol containing 5 mL water at reflux. Over a period of 15 minutes, 12.0 g (0.044 mol) of CF3CCl=CHCH2I was added drop-wise and reflux continued for an additional 0.5 hour. The cooled mixture was poured into 125 mL water, and extracted with 2×50 mL methylene chloride. The combined organic layers were concentrated at the rotovap, and the residue treated with 10 mL 5% aq. NaOH at 90° C. for 1 hour. The solution was neutralized, taken up in methylene chloride, dried, and distilled. There was thus obtained 5.5 g of greater than 96% pure $CF_3CCl=CHCH_2CH_2C(=O)CH_3$, b.p. 75–78° C. at Hg. IR (cm$^{-1}$): 1720; 1663. $^{19}$F NMR: −69.6 ppm. $^1$H NMR: δ 6.5 (1H); 2.7 (2H); 2.5 (2H); 2.2 (3H).

EXAMPLE 3

Preparation of N-(4,4,4-trifluoro-3-chloro-2-butenyl-N-t-butylamine ($CF_3CCl=CHCH_2NHtBu$)

A solution of 17.9 g (0.1 mol) $CF_3CCl=CHCH_2Cl$, 21 mL (0.2 mol) t-butyl amine, 60 mL ether, and 40 mL DMF were stirred at room temperature for 65 hours. The reaction mixture was poured into 100 mL 0.1 N NaOH. The ether layer was separated, washed with 50 mL water, 25 mL brine, and dried ($Na_2SO_4$). Distillation gave 8.5 g (39% yield) of $CF_3CCl=CHCH_2NHtBu$, b.p., 50–52° C. at 10 mm Hg. $^1$H NMR: δ 6.57 (1H); 3.48 (2H); 0.9–1.2 (10H). $^{19}$F NMR: −70.0 ppm. Analysis: Calc. For $C_8H_{13}ClF_3N$ (215.65): C, 44.55; H, 6.08; N, 6.49%. Found: C, 44.42; H, 6.11; N, 6.32%.

EXAMPLE 4

Preparation of N-(4,4,4-trifluorobuten lidene)-t-butylamine ($CF_3CH=CHCH=NtBu$)

A mixture of 16.1 g (0.09 mol) $CF_3CCl_2CH=CH_2$ (note: this is an isomer of $CF_3CCl=CHCH_2Cl$, which, along with $CF_3CHClCH=CHCl$, can also be used; the preparation of these other HCFC-1343 isomers are described in M. Van Der Puy et al., J. Fluorine Chem., 76 (1996), 49) and 24.8 g t-butylamine in 50 mL DMF was stirred at room temperature for 5.5 days. The mixture was poured into 300 mL water, extracted with 3×25 mL $CH_2Cl_2$, and the combined organic layers washed with 25 mL each of water and brine, and dried (Na2SO$_4$). Distillation provided 7.2 g (45% yield) of CF$_3$CH=CHCH=NtBu, b.p. 50° C. at 30 mm Hg. $^1$H NMR: δ 1.24 (9H); 6.13 (1H); 6.91 (1H); 7.94 (1H). $^{19}$F NMR: −65.4 ppm. IR (cm$^{-1}$): 1667; 1630. MS (Cl): 180 (M+1).

Other embodiments of this invention will be apparent to those skilled in the art from a consideration of this specification or practice of the invention herein.

What is claimed is:

1. A compound of the formula

wherein R is (Cl)=CHCH$_2$SO$_2$Ph, (Cl)=CHCH$_2$CH$_2$C(=O)CH$_3$, (Cl)=CHCH$_2$CH(COCH$_3$)$_2$, (Cl)=CHCH$_2$NR'R" or H=CHCH=NR'; R' and R" are the same or different and are selected from the group consisting of hydrogen, unsubstituted or substituted C$_1$ to C$_6$ straight chain or branched alkyl, unsubstituted or substituted C$_3$ to C$_7$ cycloalkyl, unsubstituted or substituted C$_2$ to C$_{12}$ alkenyl, a benzyl group unsubstituted or substituted with R'", a phenyl group unsubstituted or substituted with R'" or R' and R" taken together form a five- or six-membered ring; and R'" is an unsubstituted or substituted C$_1$ to C$_6$ straight chain or branched alkyl, an unsubstituted or substituted C$_1$ to C$_6$ alkoxy, an unsubstituted or substituted C$_1$ to C$_6$ thioakyl, a cyano, a halogen, or a C$_1$ to C$_2$ dialkylamino group; with the proviso that when the alkyl, cycloalkyl or alkenyl of R' or R" or the alkyl, alkoxy or thioalkyl of R'" is substituted, it may be substituted with any group compatible with amine functionality.

2. The compound according to claim 1 wherein R is (Cl)=CHCH$_2$SO$_2$Ph.

3. The compound according to claim 1 wherein R is (Cl)=CHCH$_2$CH$_2$C(=O)CH$_3$.

4. The compound according to claim 1 wherein R is (Cl)=CHCH$_2$CH(COCH$_3$)$_2$.

5. The compound according to claim 1 wherein R is (Cl)=CHCH$_2$NR'R"; R' and R" are the same or different and are selected from the group consisting of hydrogen, unsubstituted or substituted C$_1$ to C$_6$ straight chain or branched alkyl, unsubstituted or substituted C$_3$ to C$_7$ cycloalkyl, unsubstituted or substituted C$_2$ to C$_{12}$ alkenyl, a benzyl group unsubstituted or substituted with R'", a phenyl group unsubstituted or substituted with R'" or R' and R" taken together form a five- or six-membered ring; and R'" is an unsubstituted or substituted C$_1$ to C$_6$ straight chain or branched alkyl, an unsubstituted or substituted C$_1$ to C$_6$ alkoxy, an unsubstituted or substituted C$_1$ to C$_6$ thioakyl, a cyano, a halogen, or a C$_1$ to C$_2$ dialkylamino group; with the proviso that when the alkyl, cycloalkyl or alkenyl of R' or R" or the alkyl, alkoxy or thioalkyl of R'" is substituted, it may be substituted with any group compatible with amine functionality.

6. The compound according to claim 5 wherein R' is hydrogen; R" is unsubstituted or substituted C$_1$ to C$_6$ straight chain or branched alkyl; and when the alkyl of R" is substituted, it is substituted with a group that is compatible with amine functionality.

7. The compound according to claim 6 wherein the unsubstituted C$_1$ to C$_6$ straight chain or branched alkyl is selected from the group consisting of methyl, ethyl, propyl, isopropyl, butyl, isobutyl, sec-butyl, tert-butyl, n-amyl and n-hexyl.

8. The compound according to claim 7 wherein the unsubstituted C$_1$ to C$_6$ straight chain or branched alkyl is tert-butyl.

9. The compound according to claim 5 wherein R' is hydrogen; R" is unsubstituted or substituted C$_3$ to C$_7$ cycloalkyl; and when the cycloalkyl of R" is substituted, it is substituted with a group that is compatible with amine functionality.

10. The compound according to claim 5 wherein R' is hydrogen; R" is unsubstituted or substituted C$_2$ to C$_{12}$ alkenyl and when the alkenyl of R" is substituted, it is substituted with a group that is compatible with amine functionality.

11. The compound according to claim 5 wherein R' is hydrogen; R" is a benzyl group unsubstituted or substituted with R'"; R'" is an unsubstituted or substituted C$_1$ to C$_6$ straight chain or branched alkyl, an unsubstituted or substituted C$_1$ to C$_6$ alkoxy, an unsubstituted or substituted C$_1$ to C$_6$ thioakyl, a cyano, a halogen, or a C$_1$ to C$_2$ dialkylamino group; and when the alkyl, alkoxy or thioalkyl of R'" is substituted, it is substituted with a group that is compatible with amine functionality.

12. The compound according to claim 5 wherein R' is hydrogen; R" is a phenyl group unsubstituted or substituted with R'"; R'" is an unsubstituted or substituted C$_1$ to C$_6$ straight chain or branched alky, an unsubstituted or substituted C$_1$ to C$_6$ alkoxy, an unsubstituted or substituted C$_1$ to C$_6$ thioakyl, a cyano, a halogen, or a C$_1$ to C$_2$ dialkylamino group; and when the alkyl, alkoxy or thioalkyl of R'" is substituted, it is substituted with a group that is compatible with amine functionality.

13. The compound according to claim 5 wherein R' and R" are the same or different and are selected from the group consisting of unsubstituted or substituted C$_1$ to C$_6$ straight chain or branched alkyl, unsubstituted or substituted C$_3$ to C$_7$ cycloalkyl, unsubstituted or substituted C$_2$ to C$_{12}$ alkenyl, a benzyl group unsubstituted or substituted with R'", or a phenyl group unsubstituted or substituted with R'"; R'" is an unsubstituted or substituted C$_1$ to C$_6$ straight chain or branched alkyl, an unsubstituted or substituted C$_1$ to C$_6$ alkoxy, an unsubstituted or substituted C$_1$ to C$_6$ thioakyl, a cyano, a halogen, or a C$_1$ to C$_2$ dialkylamino group; and when the alky, cycloalkyl or alkenyl of R' or R" or the alky, alkoxy or thioalkyl of R'" is substituted, it may be substituted with any group compatible with amine functionality.

14. The compound according to claim 13 wherein R' is unsubstituted or substituted C$_1$ to C$_6$ straight chain or branched alkyl and R" is selected from the group consisting of unsubstituted or substituted C$_1$ to C$_6$ straight chain or branched alkyl, unsubstituted or substituted C$_3$ to C$_7$ cycloalkyl, unsubstituted or substituted C$_2$ to C$_{12}$ alkenyl, a benzyl group unsubstituted or substituted with R'", or a phenyl group unsubstituted or substituted with R'"; R'" is an unsubstituted or substituted C$_1$ to C$_6$ straight chain or branched alkyl, an unsubstituted or substituted C$_1$ to C$_6$ alkoxy, an unsubstituted or substituted C$_1$ to C$_6$ thioakyl, a cyano, a halogen, or a C$_1$ to C$_2$ dialkylamino group; and when the alky, cycloalkyl or alkenyl of R' or R" or the alkyl alkoxy or thioalkyl of R'" is substituted, it may be substituted with any group compatible with amine functionality.

15. The compound according to claim 13 wherein R' is unsubstituted or substituted C$_3$ to C$_7$ cycloalkyl and R" is selected from the group consisting of unsubstituted or substituted C$_1$ to C$_6$ straight chain or branched alkyl, unsubstituted or substituted C$_3$ to C$_7$ cycloalkyl, unsubstituted or substituted C$_2$ to C$_{12}$ alkenyl, a benzyl group unsubstituted or substituted with R'", or a phenyl group unsubstituted or substituted with R'"; R'" is an unsubstituted or substituted C$_1$ to C$_6$ straight chain or branched alkyl, an unsubstituted or substituted C$_1$ to C$_6$ alkoxy, an unsubstituted or substituted $C_1$ to $C_6$ thioakyl, a cyano, a halogen, or a $C_1$ to $C_2$ dialkylamino group; when the alkyl, cycloalkyl or alkenyl of R' or R" or the alkyl, alkoxy or thioalkyl of R'" is substituted, it may be substituted with any group compatible with amine functionality.

16. The compound according to claim 13 wherein R' is unsubstituted or substituted $C_2$ to $C_{12}$ alkenyl and R" is selected from the group consisting of unsubstituted or substituted $C_1$ to $C_6$ straight chain or branched allyl, unsubstituted or substituted $C_3$ to $C_7$ cycloalkyl, unsubstituted or substituted $C_2$ to $C_{12}$ alkenyl, a benzyl group unsubstituted or substituted with R'" or a phenyl group unsubstituted or substituted with R'"; R'" is an unsubstituted or substituted $C_1$ to $C_6$ straight chain or branched alkyl, an unsubstituted or substituted $C_1$ to $C_6$ alkoxy, an unsubstituted or substituted $C_1$ to $C_6$ thioakyl, a cyano, a halogen, or a $C_1$ to $C_2$ dialkylamino group; and when the alkyl, cycloalkyl or alkenyl of R' or R" or the alkyl, alkoxy or thioalkyl of R'" is substituted, it may be substituted with any group compatible with amine functionality.

17. The compound according to claim 13 wherein R' is a benzyl group unsubstituted or substituted with R'" and R" is selected from the group consisting of unsubstituted or substituted $C_1$ to $C_6$ straight chain or branched alkyl, unsubstituted or substituted $C_3$ to $C_7$ cycloalkyl, unsubstituted or substituted $C_2$ to $C_{12}$ alkenyl, a benzyl group unsubstituted or substituted with R'", or a phenyl group unsubstituted or substituted with R'"; R'" is an unsubstituted or substituted $C_1$ to $C_6$ straight chain or branched alkyl, an unsubstituted or substituted $C_1$ to $C_6$ alkoxy, an unsubstituted or substituted $C_1$ to $C_6$ thioakyl, a cyano, a halogen, or a $C_1$ to $C_2$ dialkylamino group; and when the alkyl, cycloalkyl or alkenyl of R' or R" or the alkyl, alkoxy or thioalkyl of R'" is substituted, it may be substituted with any group compatible with amine functionality.

18. The compound according to claim 13 wherein R' is a phenyl group unsubstituted or substituted with R'" and R" is selected from the group consisting of unsubstituted or substituted $C_1$ to $C_6$ straight chain or branched alkyl, unsubstituted or substituted $C_3$ to $C_7$ cycloalkyl, unsubstituted or substituted $C_2$ to $C_{12}$ alkenyl, a benzyl group unsubstituted or substituted with R'", or a phenyl group unsubstituted or substituted with R'"; R'" is an unsubstituted or substituted $C_1$ to $C_6$ straight chain or branched alkyl, an unsubstituted or substituted $C_1$ to $C_6$ alkoxy, an unsubstituted or substituted $C_1$ to $C_6$ thioakyl, a cyano, a halogen, or a $C_1$ to $C_2$ dialkylamino group; and when the alkyl, cycloalkyl or alkenyl of R' or R" or the alkyl, alkoxy or thioallyl of R'" is substituted, it may be substituted with any group compatible with amine functionality.

19. The compound according to claim 1 wherein R is H=CHCH=NR'; R' is selected from the group consisting of unsubstituted or substituted $C_1$ to $C_6$ straight chain or branched alkyl, unsubstituted or substituted $C_3$ to $C_7$ cycloalkyl, unsubstituted or substituted $C_2$ to $C_{12}$ alkenyl, a benzyl group unsubstituted or substituted with R'", or a phenyl group unsubstituted or substituted with R'"; and R'" is an unsubstituted or substituted $C_1$ to $C_6$ straight chain or branched alkyl, an unsubstituted or substituted $C_1$ to $C_6$ alkoxy, an unsubstituted or substituted $C_1$ to $C_6$ thioakyl, a cyano, a halogen, or a $C_1$ to $C_2$ dialkylamino group; and when the alkyl, cycloalkyl or alkenyl of R' or alkyl, alkoxy or thioalkyl of R'" is substituted, it is substituted with group that is compatible with amine functionality.

20. The compound according to claim 19 wherein R is H=CHCH=NR'; R' is unsubstituted or substituted $C_1$ to $C_6$ straight chain or branched alkyl; and when the alkyl of R' is substituted, it is substituted with group that is compatible with amine functionality.

21. The compound according to claim 20 wherein the unsubstituted $C_1$ to $C_6$ straight chain or branched alkyl is selected from the group consisting of methyl, ethyl, propyl, isopropyl, butyl, isobutyl, sec-butyl, tert-butyl, n-amyl and n-hexyl.

22. The compound according to claim 21 wherein the unsubstituted $C_1$ to $C_6$ straight chain or branched alkyl is tert-butyl.

23. The compound according to claim 19 wherein R is H=CHCH=NR'; R' is unsubstituted or substituted $C_3$ to $C_7$ cycloalkyl; and when the cycloalkyl of R' is substituted, it is substituted with group that is compatible with amine functionality.

24. The compound according to claim 19 wherein R is H=CHCH=NR'; R' is unsubstituted or substituted $C_2$ to $C_{12}$ alkenyl; and when the alkenyl of R' is substituted, it is substituted with group that is compatible with amine functionality.

25. The compound according to claim 19 wherein R is H=CHCH=NR'; R' is a benzyl group unsubstituted or substituted with R'"; R'" is an unsubstituted or substituted $C_1$ to $C_6$ straight chain or branched alkyl, an unsubstituted or substituted $C_1$ to $C_6$ alkoxy, an unsubstituted or substituted $C_1$ to $C_6$ thioakyl, a cyano, a halogen, or a $C_1$ to $C_2$ dialkylamino group; and when the alkyl, alkoxy or thioallyl of R'" is substituted, it is substituted with group that is compatible with amine functionality.

26. The compound according to claim 19 wherein R is H=CHCH=NR'; R' is a phenyl group unsubstituted or substituted with R'"; R'" is an unsubstituted or substituted $C_1$ to $C_6$ straight chain or branched alkyl, an unsubstituted or substituted $C_1$ to $C_6$ alkoxy, an unsubstituted or substituted $C_1$ to $C_6$ thioakyl, a cyano, a halogen, or a $C_1$ to $C_2$ dialkylamino group; and when the alkyl, alkoxy or thioalkyl of R'" is substituted, it is substituted with group that is compatible with amine functionality.

* * * * *